(12) United States Patent
Shuros et al.

(10) Patent No.: US 10,827,978 B2
(45) Date of Patent: Nov. 10, 2020

(54) IMPEDANCE-BASED FAR-FIELD SUBTRACTION OF WAVEFORM USING NON-TISSUE CONTACTING ELECTRODES

(71) Applicant: Boston Scientific Scimed Inc., Maple Grove, MN (US)

(72) Inventors: Allan C. Shuros, St. Paul, MN (US); Matthew S. Sulkin, New Brighton, MN (US); Jacob I. Laughner, St. Paul, MN (US); Vasiliy E. Buharin, Arlington, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 321 days.

(21) Appl. No.: 16/111,385

(22) Filed: Aug. 24, 2018

(65) Prior Publication Data

US 2019/0150842 A1 May 23, 2019

Related U.S. Application Data

(60) Provisional application No. 62/590,016, filed on Nov. 22, 2017.

(51) Int. Cl.
*A61B 5/00* (2006.01)
*A61B 18/14* (2006.01)
(Continued)

(52) U.S. Cl.
CPC .......... *A61B 5/6885* (2013.01); *A61B 5/0245* (2013.01); *A61B 5/02444* (2013.01);
(Continued)

(58) Field of Classification Search
CPC . A61B 5/02444; A61B 5/0245; A61B 5/6852; A61B 5/6858; A61B 5/6885; A61B 18/1492
See application file for complete search history.

(56) References Cited

U.S. PATENT DOCUMENTS 8,050,750 B2 11/2011 Jackson
8,812,093 B2 8/2014 Gutfinger et al.
(Continued)

OTHER PUBLICATIONS

Haddad, M. E., et al. (2013). Algorithmic detection of the beginning and end of bipolar electrograms: Implications for novel methods to assess local activation time during atrial tachycardia. Biomedical Signal Processing and Control 8:981-991.

Stevenson, W. G. and Soejima, K. (2005). Recording techniques for clinical electrophysiology. Journal of Cardiovascular Electrophysiology, Techniques and Technology, vol. 16., pp. 1017-1022.

(Continued)

*Primary Examiner* — Max F Hindenburg
(74) *Attorney, Agent, or Firm* — Faegre Drinker Biddle & Reath LLP

(57) ABSTRACT

A medical system for removing far-field signals from a unipolar electrical signal is disclosed. In embodiments, the medical system comprises a catheter and a processing device communicatively coupled to the catheter. The catheter comprises a plurality of electrodes configured to sense a plurality of unipolar signals transmitted through tissue. The processing device is configured to: receive the sensed unipolar electrical signals, determine an electrode having a high level of contact with the tissue, and determine an electrode having a lower level of contact with the tissue than the electrode having the high level of contact with the tissue. Further, the processing device is configured to determine a sensed near-field electrical signal based on the unipolar electrical signal received from the electrode having the high level of contact and the unipolar electrical signal received from the electrode having the lower level of contact.

20 Claims, 4 Drawing Sheets

(51) Int. Cl.
*A61B 5/0245* (2006.01)
*A61B 5/024* (2006.01)
*A61B 18/00* (2006.01)
*A61B 90/00* (2016.01)

(52) U.S. Cl.
CPC .......... *A61B 5/6852* (2013.01); *A61B 5/6858* (2013.01); *A61B 18/1492* (2013.01); *A61B 2018/00029* (2013.01); *A61B 2018/00351* (2013.01); *A61B 2018/00577* (2013.01); *A61B 2018/00702* (2013.01); *A61B 2018/00791* (2013.01); *A61B 2018/00839* (2013.01); *A61B 2018/00875* (2013.01); *A61B 2090/065* (2016.02); *A61B 2218/002* (2013.01); *A61B 2562/0257* (2013.01); *A61B 2562/0271* (2013.01)

(56) References Cited

U.S. PATENT DOCUMENTS

| | | | |
|---|---|---|---|
| 8,894,589 B2* | 11/2014 | Leo | A61B 90/96 600/587 |
| 8,986,214 B2* | 3/2015 | Shachar | A61B 5/062 600/508 |
| 8,998,826 B2* | 4/2015 | Hauck | A61B 18/1492 600/587 |
| 9,014,814 B2* | 4/2015 | McCarthy | A61B 18/1233 607/102 |
| 9,089,276 B2 | 7/2015 | Xi et al. | |
| 9,211,094 B2* | 12/2015 | Ludwin | A61B 90/06 |
| 9,421,061 B2 | 8/2016 | Ben Zriham et al. | |
| 9,439,578 B2 | 9/2016 | Thakur et al. | |
| 9,498,146 B2 | 11/2016 | Harlev et al. | |
| 9,820,695 B2* | 11/2017 | Cohen | A61B 5/062 |
| 9,974,608 B2* | 5/2018 | Gliner | A61B 18/1492 |
| 2012/0035495 A1 | 2/2012 | Gutfinger et al. | |

OTHER PUBLICATIONS

Tedrow, U. B. and Stevenson, W. G. (2011). Recording and interpreting unipolar electrograms to guide cathete ablation. Heart Rhythm, 8(5), pp. 791-796.

* cited by examiner

IMPEDANCE-BASED FAR-FIELD SUBTRACTION OF WAVEFORM USING NON-TISSUE CONTACTING ELECTRODES

CROSS-REFERENCE TO RELATED APPLICATION

This application claims priority to Provisional Application No. 62/590,016, filed Nov. 22, 2017, which is herein incorporated by reference in its entirety.

TECHNICAL FIELD

The present invention relates to devices and methods for determining one or more physiological parameters of a subject. More specifically, the invention relates to devices, systems, and methods for sensing physiological signals and determining a near-field component of the sensed physiological signals using non-tissue contacting electrodes.

BACKGROUND

Physicians and other medical professionals use electrodes disposed on mapping catheters to sense physiological signals of tissue. The sensed physiological signals are used to determine the health of the tissue.

Two different sensing methods are generally used for sensing physiological signals, unipolar sensing and bipolar sensing. Unipolar sensing uses one electrode (e.g., the cathode) in contact with, or in close proximity to, tissue and another electrode (e.g., the anode) outside of the tissue that is being sensed. For bipolar sensing, both electrodes (i.e., the cathode and anode) are in contact with, or in close proximity to, the tissue that is being sensed.

SUMMARY

Embodiments disclosed herein determine and remove far-field signals present in sensed unipolar electrical signals by using the signals sensed by non-contact or partially-contacting electrodes.

In an Example 1, a medical system for removing far-field signals from a unipolar electrical signal comprises: a catheter comprising a plurality of electrodes, each electrode being configured to sense unipolar electrical signals transmitted through tissue; and a processing device communicatively coupled to the catheter, the processing device configured to: receive the sensed unipolar electrical signals; determine an electrode of the plurality of electrodes having a high level of contact with the tissue; determine an electrode of the plurality of electrodes having a lower level of contact with the tissue than the electrode having the high level of contact with the tissue; determine a sensed near-field electrical signal based on the unipolar electrical signal received from the electrode having the high level of contact and the unipolar electrical signal received from the electrode having the lower level of contact; and output the determined near-field electrical signal to a display device.

In an Example 2, the medical system of Example 1, wherein the electrode of the plurality of electrodes having a lower level of contact comprises more than one electrode of the plurality of electrodes and wherein the processing device is further configured to average the unipolar electrical signals received from the more than one electrode having the lower level of contact.

In an Example 3, the medical system of Example 2, wherein to average the unipolar electrical signals received from the more than one electrode having the lower level of contact, the processing device is configured to assign weights to each of the unipolar electrical signals received from the more than one electrode having the lower level of contact and average the weighted unipolar electrical signals.

In an Example 4, the medical system of Example 3, the processing device further configured to determine impedances associated with each electrode of the plurality of electrodes and wherein the weights assigned to the unipolar electrical signals are based on the respective determined impedances associated with each electrode.

In an Example 5, the medical system of Example 4, wherein the weights have a linear relationship with the respective determined impedances.

In an Example 6, the medical system of any of Examples 2-5, wherein to determine the sensed near-field electrical signal, the processing device is configured to subtract the averaged unipolar electrical signal from the unipolar electrical signal received from the electrode having the high level of contact.

In an Example 7, the medical system of any of Examples 1-6, wherein the processing device is configured to: determine an electrode's level of contact with the tissue based on at least one of: amplitude of the sensed unipolar electrical signal, measured impedance, sensed temperature, determined mechanical force, and proximity to a proximity sensor of the catheter.

In an Example 8, the medical system of Example 7, wherein the processing device is configured to: accept or reject a sensed signal based on the determined electrode's level of contact; and include only the accepted signals in an electro-anatomical map.

In an Example 9, a method removing far-field signals from a unipolar electrical signal comprises: receiving sensed unipolar electrical signals from a plurality of electrodes disposed on a distal end of a catheter, wherein the unipolar electrical signals are transmitted through tissue; determining an electrode of the plurality of electrodes having a high level of contact with the tissue; determine an electrode of the plurality of electrodes having a lower level of contact with the tissue than the electrode having the high level of contact with the tissue; determine a sensed near-field electrical signal based on the unipolar electrical signal received from the electrode having the high level of contact and the unipolar electrical signal received from the electrode having the lower level of contact; and output the determined near-field electrical signal to a display device.

In an Example 10, the method of Example 9, wherein the electrode of the plurality of electrodes having a lower level of contact comprises more than one electrode of the plurality of electrodes and the method further comprising averaging the unipolar electrical signals received from the more than one electrode having the lower level of contact.

In an Example 11, the method of Example 10, wherein averaging the unipolar electrical signals received from the more than one electrode having the lower level of contact comprises assigning weights to each of the unipolar electrical signals received from the more than one electrode having the lower level of contact and average the weighted unipolar electrical signals.

In an Example 12, the method of Example 11, further comprising determining impedances associated with each electrode of the plurality of electrodes and wherein the weights assigned to the unipolar electrical signals are based on the respective determined impedances associated with each electrode.

In an Example 13, the method of any of Examples 10-12, wherein determining the sensed near-field electrical signal comprises subtracting the averaged unipolar electrical signal from the unipolar electrical signal received from the electrode having the high level of contact.

In an Example 14, the method of any of Examples 9-13, further comprising: determining an electrode's level of contact with the tissue based on at least one of: amplitude of the sensed unipolar electrical signal, measured impedance, sensed temperature, determined mechanical force, and proximity to a proximity sensor of the catheter.

In an Example 15, the method of Example 14, wherein an electrode having the high level of contact is the electrode having a higher impedance than other electrodes of the plurality of electrodes.

In an Example 16, a medical system for removing far-field signals from a unipolar electrical signal comprises: a catheter comprising a plurality of electrodes, each electrode being configured to sense unipolar electrical signals transmitted through tissue; and a processing device communicatively coupled to the catheter, the processing device configured to: receive the sensed unipolar electrical signals; determine an electrode of the plurality of electrodes having a high level of contact with the tissue; determine an electrode of the plurality of electrodes having a lower level of contact with the tissue than the electrode having the high level of contact with the tissue; determine a sensed near-field electrical signal based on the unipolar electrical signal received from the electrode having the high level of contact and the unipolar electrical signal received from the electrode having the lower level of contact; and output the determined near-field electrical signal to a display device.

In an Example 17, the medical system of Example 16, wherein the electrode of the plurality of electrodes having a lower level of contact comprises more than one electrode of the plurality of electrodes and wherein the processing device is further configured to average the unipolar electrical signals received from the more than one electrode having the lower level of contact.

In an Example 18, the medical system of Example 17, wherein to average the unipolar electrical signals received from the more than one electrode having the lower level of contact, the processing device is configured to assign weights to each of the unipolar electrical signals received from the more than one electrode having the lower level of contact and average the weighted unipolar electrical signals.

In an Example 19, the medical system of Example 18, the processing device further configured to determine impedances associated with each electrode of the plurality of electrodes and wherein the weights assigned to the unipolar electrical signals are based on the respective determined impedances associated with each electrode.

In an Example 20, the medical system of Example 19, wherein the weights have a linear relationship with the respective determined impedances.

In an Example 21, the medical system of Example 17, wherein to determine the sensed near-field electrical signal, the processing device is configured to subtract the averaged unipolar electrical signal from the unipolar electrical signal received from the electrode having the high level of contact.

In an Example 22, the medical system of Example 16, wherein the processing device is configured to: determine an electrode's level of contact with the tissue based on at least one of: amplitude of the sensed unipolar electrical signal, measured impedance, sensed temperature, determined mechanical force, and proximity to a proximity sensor of the catheter.

In an Example 23, the medical system of Example 22, wherein the processing device is configured to: accept or reject a sensed signal based on the determined electrode's level of contact; and include only the accepted signals in an electro-anatomical map.

In an Example 24, a method removing far-field signals from a unipolar electrical signal comprises: receiving sensed unipolar electrical signals from a plurality of electrodes disposed on a distal end of a catheter, wherein the unipolar electrical signals are transmitted through tissue; determining an electrode of the plurality of electrodes having a high level of contact with the tissue; determine an electrode of the plurality of electrodes having a lower level of contact with the tissue than the electrode having the high level of contact with the tissue; determine a sensed near-field electrical signal based on the unipolar electrical signal received from the electrode having the high level of contact and the unipolar electrical signal received from the electrode having the lower level of contact; and output the determined near-field electrical signal to a display device.

In an Example 25, the method of Example 24, wherein the electrode of the plurality of electrodes having a lower level of contact comprises more than one electrode of the plurality of electrodes and the method further comprising averaging the unipolar electrical signals received from the more than one electrode having the lower level of contact.

In an Example 26, the method of Example 25, wherein averaging the unipolar electrical signals received from the more than one electrode having the lower level of contact comprises assigning weights to each of the unipolar electrical signals received from the more than one electrode having the lower level of contact and average the weighted unipolar electrical signals.

In an Example 27, the method of Example 26, further comprising determining impedances associated with each electrode of the plurality of electrodes and wherein the weights assigned to the unipolar electrical signals are based on the respective determined impedances associated with each electrode.

In an Example 28, the method of Example 27, wherein the weights have a linear relationship with the respective determined impedances.

In an Example 29, the method of Example 25, wherein determining the sensed near-field electrical signal comprises subtracting the averaged unipolar electrical signal from the unipolar electrical signal received from the electrode having the high level of contact.

In an Example 30, the method of Example 24 further comprising: determining an electrode's level of contact with the tissue based on at least one of: amplitude of the sensed unipolar electrical signal, measured impedance, sensed temperature, determined mechanical force, and proximity to a proximity sensor of the catheter.

In an Example 31, the method of Example 30, wherein the electrode having the high level of contact is the electrode having a higher impedance than other electrodes of the plurality of electrodes.

In an Example 32, a non-transitory computer-readable medium comprises executable instructions that when executed by one or more processors of a medical system cause the one or more processors to: receive sensed unipolar electrical signals from a plurality of electrodes disposed on a distal end of a catheter, wherein the unipolar electrical signals are transmitted through tissue; determine an impedance associated with each electrode of the plurality of electrodes; determine, using the determined impedances, an electrode of the plurality of electrodes having a high level of contact with the tissue; determine, using the determined impedances, an electrode of the plurality of electrodes having a lower level of contact with the tissue than the electrode having the high level of contact with the tissue; determine, using the unipolar electrical signal sensed by the electrode having the lower level of contact, a far-field component of the unipolar electrical signal sensed by the electrode having a high level of contact; remove the far-field component of the unipolar electrical signal sensed by the electrode having the high level of contact to determine the near-field component of the unipolar electrical signal sensed by the electrode having the high level of contact; and output the determined near-field electrical signal to a display device.

In an Example 33, the non-transitory computer-readable medium of Example 32, wherein the electrode of the plurality of electrodes having a lower level of contact comprises more than one electrode of the plurality of electrodes and wherein the executable instructions comprise instructions that cause the one or more processors to: average the unipolar electrical signals received from the more than one electrode having the lower level of contact.

In an Example 34, the non-transitory computer-readable medium of Example 33, wherein to average the unipolar electrical signals received from the more than one electrode having the lower level of contact, the executable instructions comprise instructions that cause the one or more processors to: assign weights to each of the unipolar electrical signals received from the more than one electrode having the lower level of contact and average the weighted unipolar electrical signals.

In an Example 35, the non-transitory computer-readable medium of Example 34, wherein the weights have a linear relationship with the respective determined impedances.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
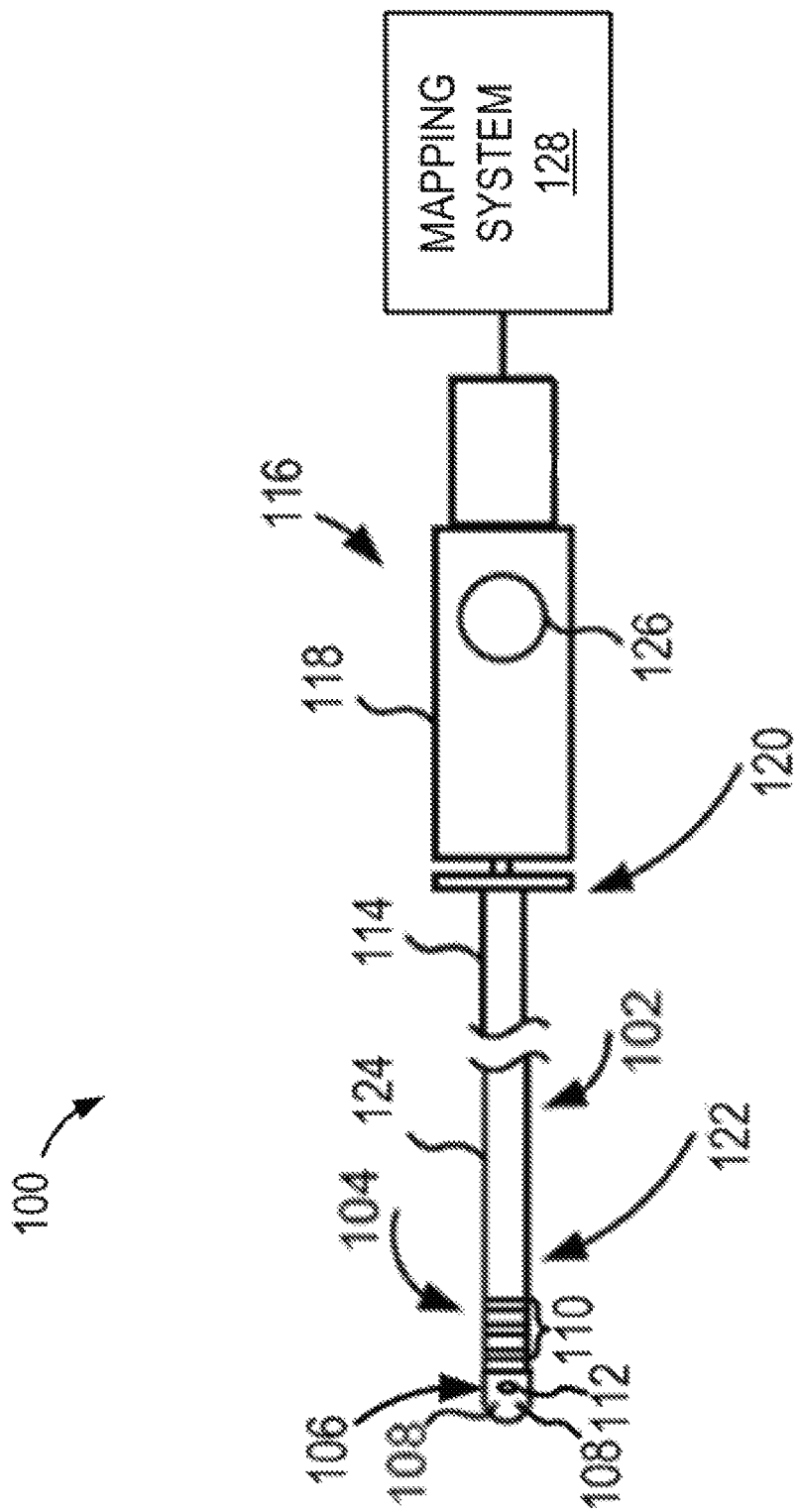
FIG. 1 depicts an illustrative medical system for removing far-field signals present in unipolar signals, in accordance with embodiments disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

As stated above, two different sensing methods are generally used for sensing physiological signals, unipolar sensing and bipolar sensing. Both unipolar and bipolar sensing methods, however, have drawbacks that impact their ability to accurately sense physiological signals. With regard to unipolar sensing, because unipolar sensing has one electrode in contact with or in close proximity to tissue and another electrode outside of the tissue that is being sensed, an antenna effect may be created where the sensed signal includes a lot of extraneous information, for example, breathing, far-field signals originating from non-proximal tissue and/or the like. For example, when sensing ventricular activity, far-field signals originating from the atrium may be present in the sensed signals when using the unipolar sensing method. On the other hand, bipolar sensing has reduced spatial and temporal resolution in comparison to unipolar sensing. Embodiments disclosed herein provide solutions to some of these issues.

FIG. 1 depicts an illustrative medical system 100 for removing far-field effects present in unipolar sensing using non-tissue contacting electrodes, in accordance with embodiments of the disclosure. The medical system 100 includes a catheter 102 having a tip assembly 104. The tip assembly 104 may include a tissue ablation electrode 106, mapping electrodes 108, ring electrodes 110, and a sensor 112. The catheter 102 also includes a catheter body 114 and a proximal catheter handle assembly 116, having a handle 118, coupled to a proximal end 120 of the catheter body 114. The tip assembly 104 is coupled to a distal end 122 of the catheter body 114.

In embodiments, the medical system 100 may be utilized in mapping and/or ablation procedures on a subject. The subject may be a human, a dog, a pig, and/or any other animal having physiological parameters that can be recorded. In various embodiments, the catheter 102 may be configured to be introduced into or through the vasculature of a subject and/or into or through any other lumen or cavity. In an example, the catheter 102 may be inserted through the vasculature of the subject, into one or more chambers of the subject's heart (e.g., a target area), and/or other organ of the subject.

When the catheter 102 is inserted in the subject's vasculature, heart or other organ, the tissue ablation electrode 106 may be configured to apply ablation energy to the subject's tissue. According to embodiments, the tissue ablation electrode 106 may be, or be similar to, any number of different tissue ablation electrodes such as, for example, the IntellaTip MiFi,™ Orion™ or the Blazer™ Ablation tip, all of which are available from Boston Scientific of Marlborough, Mass. In embodiments, the tissue ablation electrode 106 may have any number of different sizes, shapes, and/or other configuration characteristics. The tissue ablation electrode 106 may be any length and may have any number of the mapping electrodes 108 positioned therein and spaced circumferentially and/or longitudinally about the tissue ablation electrode 106. In some instances, the tissue ablation electrode 106 may have a length of between one (1) mm and twenty (20) mm, three (3) mm and seventeen (17) mm, or six (6) mm and fourteen (14) mm. In an illustrative example, the tissue ablation electrode 106 may have an axial length of about eight (8) mm. In another illustrative example, the tissue ablation electrode 106 may include an overall length of approximately 4-10 mm. In embodiments, the tissue ablation electrode 106 may include an overall length of approximately 4 mm, 4.5 mm, and/or any other desirable length. In some cases, the plurality of mapping electrodes 108 may be spaced at any interval about the circumference of the tissue ablation electrode 106. In an example, the tissue ablation electrode 106 may include at least three mapping electrodes 108 equally or otherwise spaced about the circumference of the tissue ablation electrode 106 and at the same or different longitudinal positions along the longitudinal axis of the tissue ablation electrode 106.

Additionally or alternatively, when inserted into the subject's vasculature, heart or other organ, the mapping electrodes 108 and/or the ring electrodes 110 may be used to sense electrophysiological signals transmitted through tissue and/or map tissue based on the sensed signals. In embodiments, the mapping electrodes 108 may be configured to operate in unipolar and/or bipolar sensing modes. In embodiments, one or more of the mapping electrodes 108 may form a unipolar pair with an electrode (not shown) external to the subject's vasculature and/or heart. For example, one or more of the mapping electrodes may form a unipolar pair with an electrode included in a patch attached to a subject's back. Additionally or alternatively, the mapping electrodes 108 may define and/or at least partially form one or more bipolar electrode pairs with each other. Each unipolar and/or bipolar electrode pair may be configured to measure an electrical signal corresponding to a sensed electrical activity (e.g., an electrogram (EGM) reading) of the myocardial tissue proximate thereto. In embodiments, one or more of the mapping electrodes 108 and/or one or more of the ring electrodes 110 may form one or more pairs and the signals therefrom may be transmitted to a mapping system 128 to determine the contact and orientation of the tip assembly 104 relative to a subject's tissue, as explained in more detail below in relation to FIG. 3. Furthermore, based on the contact and orientation of the tip assembly 104 relative to the subject's tissue, the mapping system 128 may determine far-field signals included in the unipolar signals and remove the far-field signals from the unipolar signals, as described in more detail below in relation to FIG. 4. Additionally or alternatively, an EGM reading or signal from a unipolar and/or bipolar electrode pair may at least partially form the basis of a contact assessment, ablation area assessment (e.g., tissue viability assessment), and/or an ablation progress assessment (e.g., a lesion formation/maturation analysis).

Additionally or alternatively, the tip assembly 104 may include one or more sensors 112. In embodiments, the sensors 112 may be a sensor for measuring force, temperature and/or proximity relative to other portions of the catheter (e.g., electrodes of the catheter) in embodiments where the catheter is a basket catheter. In embodiments, the sensors 112 may be used to determine tissue contact, as explained in more detail below in relation to FIGS. 3 and 4.

In embodiments, the tip assembly 104 may include one or more irrigation ports (not shown). In embodiments, the irrigation ports may contribute to reducing coagulation of blood near the tip assembly 104. For example, when the tissue ablation electrode 106 is applying ablation energy to cardiac tissue, a mapping system 128 may provide cooling fluid, such as a saline, through the catheter 102 and out through the irrigation ports in order to cool the blood. In embodiments, the amount of irrigation fluid provided to an irrigation port may be based on a determined fluid flow condition as described herein.

In embodiments, the catheter 102 may include a deflectable catheter region 124 configured to allow the catheter 102 to be steered through the vasculature of a subject, and which may enable the tissue ablation electrode 106 to be accurately placed adjacent a targeted tissue region. A steering wire (not shown) may be slidably disposed within the catheter body 114. The handle assembly 116 may include one or more steering members 126 such as, for example, rotating steering knobs that are rotatably mounted to the handle 118. Rotational movement of a steering member 126 relative to the handle 118 in a first direction may cause a steering wire to move proximally relative to the catheter body 114 which, in turn, may tension the steering wire, thus pulling and bending the catheter deflectable region 124 into an arc; and rotational movement of the steering member 126 relative to the handle 118 in a second direction may cause the steering wire to move distally relative to the catheter body 114 which, in turn, may relax the steering wire, thus allowing the catheter 102 to return toward its original form. To assist in the deflection of the catheter 102, the deflectable catheter region 124 may be made of a lower durometer plastic than the remainder of the catheter body 114.

According to embodiments, the catheter body 114 includes one or more cooling fluid lumens (not shown) to provide cooling fluid to an irrigation port (not shown) and may include other tubular element(s) to provide desired functionality to the catheter 102. The addition of metal in the form of a braided mesh layer sandwiched in between layers of plastic tubing may be used to increase the rotational stiffness of the catheter 102.

The illustrated medical system 100 also includes a mapping system 128. The mapping system 128 may be configured to determine and map sensed signals and control aspects of the functioning of the medical system 100 such as, for example, an RF generator, an irrigation system, a display system, and/or the like. In embodiments, the mapping system 128 may be configured to adjust one or more operation parameters based on information such as, for example, user input, input from other components, and/or the like.

Figure 2:
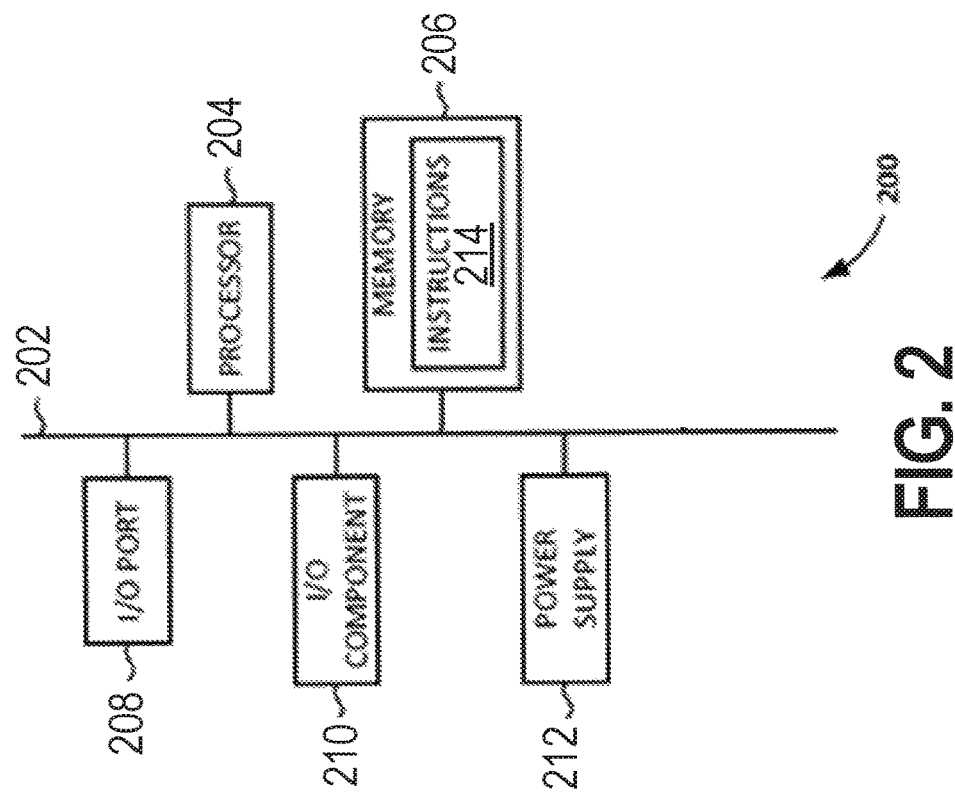
FIG. 2 is a block diagram depicting an illustrative computing device, in accordance with embodiments disclosed herein.

Any number of components of the mapping system 128 may be implemented using one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "handheld devices," "smartphones," "general-purpose graphics processing units (GPGPUs)," and the like, all of which are contemplated within the scope of FIGS. 1 and 2, with reference to various components of the mapping system 128 and/or computing device 200.

In embodiments, the computing device 200 includes a bus 202 that, directly and/or indirectly, couples the following devices: a processor 220, a memory 206, an input/output (I/O) port 208, an I/O component 210, and a power supply 212. Any number of additional components, different components, and/or combinations of components may also be included in the computing device 200. The I/O component 210 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 202 represents what may be one or more busses (such as, for example, an address bus, data bus, or combination thereof). Similarly, in embodiments, the computing device 200 may include a number of processors 204, a number of memory components 206, a number of I/O ports 208, a number of I/O components 210, and/or a number of power supplies 212. Additionally any number of these components, or combinations thereof, may be distributed and/or duplicated across a number of computing devices.

In embodiments, the memory 206 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 206 stores computer-executable instructions 214 for causing the processor 204 to implement aspects of embodiments of system components discussed herein and/or to perform aspects of embodiments of methods and procedures discussed herein.

The computer-executable instructions 214 may include, for example, computer code, machine-useable instructions, and the like such as, for example, program components capable of being executed by one or more processors 204 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative medical system 100 shown in FIG. 1 and the illustrated computing device 200 shown in FIG. 2 are not intended to suggest any limitation as to the scope of use or functionality of embodiments of the present disclosure. The illustrative medical system 100 and the illustrated computing device 200 should not be interpreted as having any dependency or requirement related to any single component or combination of components illustrated therein. Additionally, various components depicted in FIG. 1 and various components depicted in FIG. 2 may be, in embodiments, integrated with various ones of the other components depicted therein (and/or components not illustrated), all of which are considered to be within the ambit of the subject matter disclosed herein.

Figure 3:
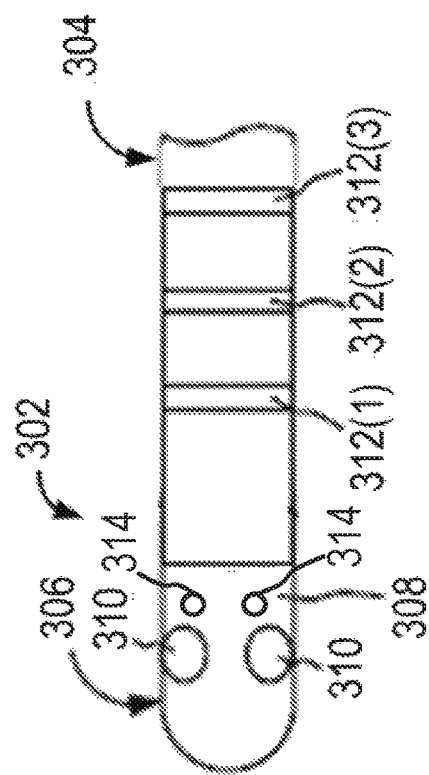
FIG. 3 depicts an illustrative catheter tip assembly, in accordance with embodiments disclosed herein.

FIG. 3 depicts an illustrative catheter tip assembly 302, in accordance with embodiments of the disclosure. The tip assembly 302 is coupled to a distal end of a catheter body 304 and includes an ablation electrode 306 having an open interior region defined by an exterior wall 308, mapping electrodes 310, ring electrodes 312 and/or one or more sensors. In the illustrated embodiment, the tip assembly 302 has a generally cylindrical shape with a semi-spherical tip, but in other embodiments, the tip assembly 302 may have any number of different shapes such as, for example, an elliptical shape, a polygonal shape, and/or the like. By way of an example and not limitation, embodiments of the tip assembly 302 may have a diameter on the order of about 0.08-0.1 inches, a length on the order of about 0.2-0.3 inches, and an exterior wall 308 with a thickness on the order of about 0.003-0.004 inches. According to embodiments, the ablation electrode 306 may be formed from a conductive material. For example, some embodiments use a platinum-iridium alloy. Some embodiments use an alloy with approximately 90% platinum and 10% iridium. The conductive material of the ablation electrode 306 may be used to conduct RF energy used to form legions during the ablation procedure. In embodiments, the tip assembly may include one or more irrigation ports (not shown) to reduce coagulation of blood near the tip assembly 302 when the ablation electrode 306 is used to form legions during an ablation procedure.

The mapping functions may be performed, at least in part, by mapping electrodes 310 and ring electrodes 312. Additionally or alternatively, the mapping electrodes 310 and the ring electrodes 312 may be used to determine tissue contact. For example, the ablation electrode 306 may transmit a current to the ring electrode 312(3), which creates a voltage therebetween. Additionally, each of the mapping electrodes may form a pair with one of the ring electrodes 312. For example, each of the mapping electrodes 310 may form a pair with the ring electrode 312(1) and a voltage may be measured between each of the mapping electrodes and the ring electrode 312(1). Based on the measured voltages, local impedances for each of the mapping electrodes can be determined. Using the determined local impedances, the tissue contact for the tip assembly 302 can be determined. For example, tissue generally has a higher impedance than blood. As such, when the tip assembly 302 is disposed into a subject's heart, if one of the mapping electrodes 310 has a higher impedance than another mapping electrode 310, then it is likely that the mapping electrode 310 exhibiting the higher impedance is in contact with tissue; and, the mapping electrode 310 exhibiting a lower impedance is only in partial contact with tissue and/or is not in contact with tissue, but is instead in located in the blood pool. Further details regarding determining tissue contact based on impedance are provided in U.S. Patent Appln. No. 62/510,189, which is expressly incorporated herein by reference in its entirety for all purposes. Once tissue contact of the tip assembly 302 is determined, a far-field signal may be determined and removed from sensed unipolar signals as described in more detail below in relation to FIG. 4.

Additionally or alternatively, the one or more sensors 314 may be used to determine tissue contact. In embodiments, the one or more sensors 314 may be force sensors and/or temperature sensors. For example, a force measured by a first force sensor 314 proximal to a first mapping electrode 310 that is higher than a force measured by a second force sensor 314 proximal to a second mapping electrode 310 may indicate the first mapping electrode 310 is in partial or complete contact with tissue whereas the second mapping electrode 310 may have no or partial contact with tissue. As another example, a temperature measured by a first temperature sensor 314 proximal to a first mapping electrode 310 that is higher than a temperature measured by a second temperature sensor 314 proximal to a second mapping electrode 310 may indicate the first mapping electrode 310 is in partial or complete contact with tissue whereas the second mapping electrode 310 may have no or partial contact with tissue. Additionally or alternatively, the one or more sensors 314 may be proximity sensors 314 (e.g., magnetic sensors) that are used to determine how close the proximity sensors 314 are to other portions of the catheter (e.g., the electrodes) in embodiments where the catheter is a basket catheter. When the basket catheter is supposed to be fully deployed and the proximity sensors 314 are used to determine portions of the basket catheter are closer than they should be, then it can be determined that those portions may be in contact with tissue.

The illustrative tip assembly 302 shown in FIG. 3 is not intended to suggest any limitation as to the scope of use or functionality of embodiments of the present disclosure. The illustrative tip assembly 302 should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the subject matter disclosed herein.

Figure 4:
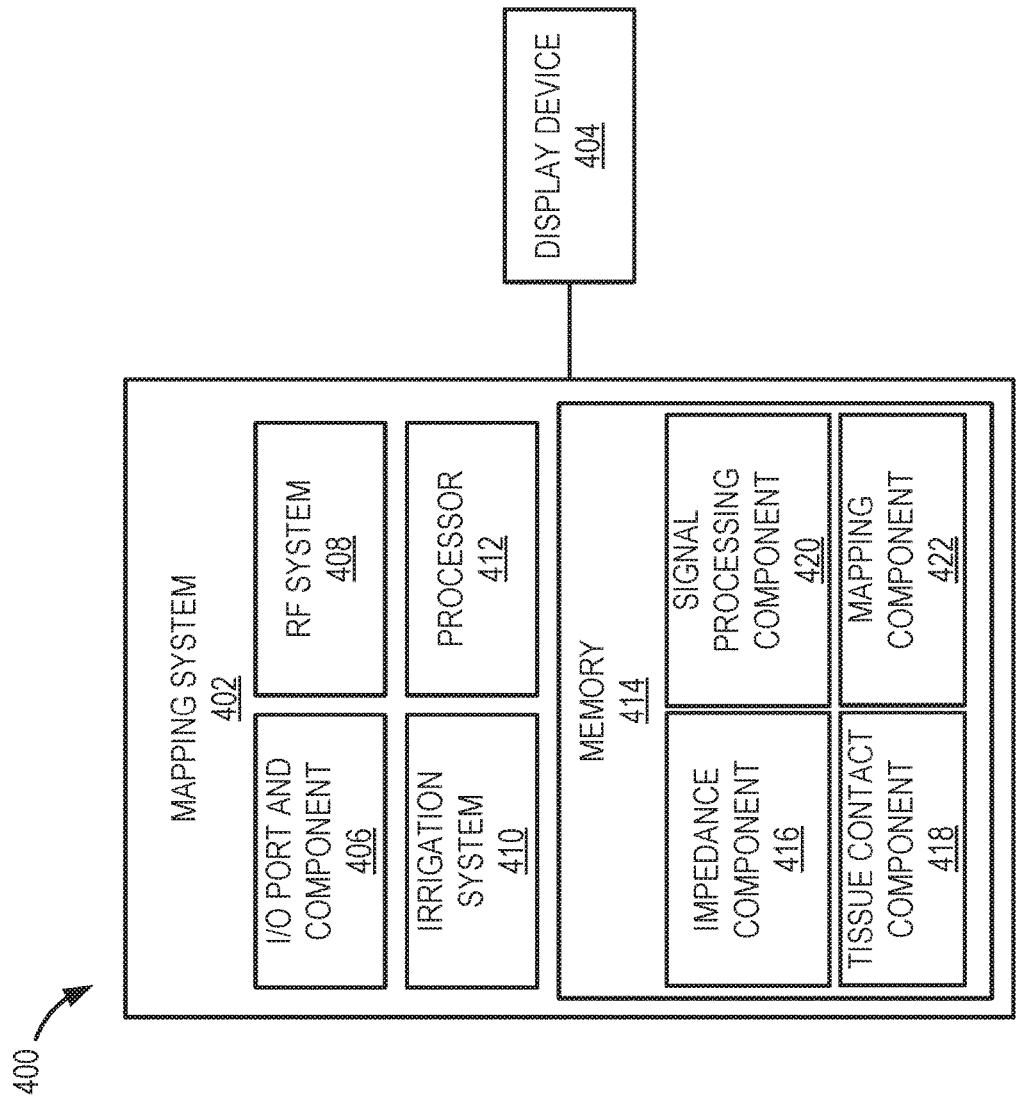
FIG. 4 is a block diagram depicting an illustrative operating environment for removing far-field signals present in unipolar signals, in accordance with embodiments disclosed herein.

FIG. 4 is a block diagram depicting an illustrative operating environment 400 for removing far-field signals present in unipolar signals, in accordance with embodiments disclosed herein. As described above, one drawback of unipolar sensing is that an antenna effect is created where the sensed signal includes a lot of extraneous information. However, the advantage of unipolar sensing has better spatial and temporal resolution than bipolar sensing. As such, the operating environment 400 uses unipolar sensing so that spatial and temporal resolution are high, but also provides embodiments, as set forth below, for effectively removing the far-field signals present in unipolar signals.

According to embodiments, the operating environment 400 may be, be similar to, include, be included in, or correspond to the mapping system 128 depicted in FIG. 1. As shown in FIG. 4, the illustrative operating environment 400 includes a mapping system 402 and a display device 404. In embodiments, the display device 404 may be incorporated into the mapping system 402. Alternatively, the display device 404 may be separate from the mapping system 402 and be communicatively coupled via an I/O port and component 406 to the mapping system 402.

In embodiments, the display device 404 may be configured to present an indication of a tissue contact, tissue condition, and/or effectiveness of an ablation procedure. Additionally or alternatively, the display device 404 may include electrocardiogram (ECG) information, which may be analyzed by a user to determine the existence and/or location of arrhythmia substrates within the heart and/or determine the location of a tip assembly within the heart, vasculature and/or organ of a subject.

As shown, the mapping system 402 includes an input/output (I/O) port and component 406 (e.g., the I/O port 208 depicted in FIG. 2 and/or the I/O component 210 depicted in FIG. 2), an RF system 408, an irrigation system 410, a processor 412 (e.g., the processor 220 depicted in FIG. 2), and memory 414 (e.g., the memory 206 depicted in FIG. 2).

The RF system 408 may be used to generate RF energy for use during an ablation procedure. The RF system 408 may include an RF source that produces the RF energy and an RF generator component that controls the timing, level, and/or other characteristics of the RF energy delivered by the RF system 408. In embodiments, the RF system 408 may be configured to deliver ablation energy to a catheter (e.g., the catheter 102 depicted in FIG. 1 and/or the tip assembly 302 depicted in FIG. 3) in a controlled manner in order to ablate the target tissue sites. Ablation of tissue within the heart is well known in the art, and thus for purposes of brevity, the RF system 408 will not be described in further detail. Further details regarding RF systems are provided in U.S. Pat. No. 5,383,874, which is expressly incorporated herein by reference in its entirety for all purposes.

In embodiments, the irrigation system 410 may include an irrigation fluid source for providing cooling fluid, such as a saline, through a catheter and out through the irrigation ports (not shown). In embodiments, the irrigation fluid source of the irrigation system 410 may include a fluid reservoir and a pump to provide cooling fluid through the catheter. The irrigation system 410 may also include an irrigation fluid output component. The irrigation fluid output component may control the timing, level, and/or other characteristics of the irrigation fluid provided by the irrigation system 410.

The processor 412 may execute instructions and perform desired tasks as specified by computer-executable instructions (e.g., the instructions 214 depicted in FIG. 2) stored in the memory 414. The processor 412 may also be configured to store information in the memory 414 and/or access information from the memory 414. For example, in embodiments, the processor 412 may be configured to store data to and/or access instructions stored on an impedance component 416, a tissue contact component 418, a signal processing component 420, a mapping component 422, and/or the like.

The memory 414 may include volatile and/or non-volatile memory, and may store instructions that, when executed by the processor 412 cause methods and processes to be performed by the mapping system 402. For example, in embodiments, the processor 412 may process instructions and/or data stored in the memory 414 to remove far-field signals from sensed unipolar signals as described below.

In embodiments, a catheter (e.g., the catheter 102 depicted in FIG. 1 and/or the tip assembly 302 depicted in FIG. 3) may be communicatively coupled to the I/O port and component 406. The I/O port and component 406 may be configured to receive one or more current signals and/or one or more voltage signals. For example, a current may be injected between a ring electrode (e.g., the ring electrodes 110 depicted in FIG. 1 and/or the ring electrodes 312 depicted in FIG. 3) and an ablation electrode (e.g., the ablation electrode 106 depicted in FIG. 1 and/or the ablation electrode 306 depicted in FIG. 3) and a signal representing the current injection may be sent to the impedance component 416. Additionally or alternatively, voltages between one or more mapping electrodes (e.g., the mapping electrodes 108 depicted in FIG. 1 and/or the mapping electrodes 310) and one or more ring electrodes (e.g., the ring electrodes 110 depicted in FIG. 1 and/or the ring electrodes 312 depicted in FIG. 3) may be transmitted to the impedance component 416. Based on the inject current and the voltages, respective impedances for each of the mapping electrodes may be determined by the impedance component 416.

In embodiments, the I/O port and component 406 may also be configured to receive one or more unipolar signals from the catheter. The received unipolar signals may then be transmitted to the tissue contact component 418. In embodiments, the tissue contact component 418 may determine whether the received unipolar signals represent stable signals. For example, the tissue contact component 418 may include determining whether it is likely the subject was moving during acquisition of the signals and/or the morphology of the signals are stable, i.e., the rhythm of the signal is stable. If the tissue contact component 418 determines either there is subject movement and/or the rhythm is not stable, the received unipolar signals may be disregarded and the tissue contact component 418 may receive new unipolar signals.

Additionally or alternatively, the tissue contact component 418 may be configured to determine which electrode(s) (e.g., the mapping electrodes 108 depicted in FIG. 1 and/or the mapping electrodes 310 depicted in FIG. 3) of a catheter are in contact with tissue. In embodiments, the tissue contact component 418 may be configured to determine which electrodes are in contact with tissue based on impedance determined by the impedance component 416. For example, a mapping electrode having a higher impedance than other mapping electrodes may be indicative of partial or complete contact with tissue. Alternatively, a mapping electrode having a lower impedance than other mapping electrodes may be indicative that the electrode is not in contact with tissue.

Additionally or alternatively, the tissue contact component 418 may determine whether one or more electrodes are in contact with tissue based on force measurements determined by one or more force sensors incorporated into a distal end of the catheter. For example, a first sensor proximal to a first mapping electrode having a higher force than a second sensor located proximal to a second mapping electrode may indicate that the first mapping electrode is in contact or in partial contact with the tissue whereas the second mapping electrode is in partial contact with tissue or not in contact with tissue.

Additionally or alternatively, the tissue contact component 418 may determine whether one or more electrodes are in contact with tissue based on an amplitude of a unipolar signal. For example, a unipolar signal sensed by a first electrode that has a higher amplitude than a unipolar signal sensed by a second electrode may indicate the first electrode is in contact or in partial contact with tissue whereas the second electrode is in partial contact with tissue or not in contact with tissue. Because different types of tissue (e.g., myocardium vs. venous) and different locations of tissue (e.g., central wall of the heart vs. outer ventricular wall) may transmit signals having different amplitudes, the tissue contact component 418 may adjust the expected amplitude based on what tissue and/or the location of the tissue that is being sensed. For example, because the central wall of the heart transmits signals having lower amplitudes than the amplitudes of the outer ventricular wall, the expected amplitude may be scaled down so that when the catheter is disposed near the central wall, the mapping electrode is not mistaken for being in contact with the blood pool as opposed to the central wall.

Additionally or alternatively, the tissue contact component 418 may determine whether one or more electrodes are in contact with tissue based on temperature measurements determined by one or more temperature sensors incorporated into a distal end of the catheter. For example, a first sensor proximal to a first mapping electrode having a higher temperature than a second sensor located proximal to a second mapping electrode may indicate that the first mapping electrode is in contact or in partial contact with the tissue whereas the second mapping electrode is in partial contact with tissue or not in contact with tissue.

Additionally or alternatively, the tissue contact component 418 may determine whether one or more electrodes are in contact with tissue based on proximity measurements determined by one or more proximity sensors incorporated into a distal end of the catheter in embodiments where the catheter is a basket catheter. For example, a first portion of the basket catheter being determined to be in closer proximity to a proximity sensor than a second portion of the basket catheter may be used to determine the first portion of the basket catheter is in contact or in partial contact with the tissue whereas the second portion of the basket catheter is in partial contact with tissue or not in contact with tissue.

Once the level of tissue contact is determined by the tissue contact component 418, the signal processing component 420 may determine a far-field component in any sensed unipolar signals. In embodiments, the signal processing component 420 may determine a non-contacting electrode to be sensing a far-field signal. Additionally or alternatively, the signal processing component 420 may determine a partially contacting electrode to be sensing at least a portion of far-field signals.

In embodiments where there is more than one non-contacting and/or partially contacting electrode, the signal processing component 420 may average the sensed signals of the non-contacting and/or partially contacting electrodes. In embodiments, the signal processing component 420 may also assign weights to each of the sensed signals of the non-contacting and/or partially contacting electrodes. The weights may be assigned based on a determined level of contact. For example, if two electrodes are determined to be non-contacting and/or partially contacting electrodes but a first electrode of the two electrodes has associated therewith a lower impedance, lower temperature, lower force and/or lower proximity to a proximity sensor than the second electrode, the signal processing component 420 may assign a higher weight to the first electrode than the second electrode of the two electrodes.

In embodiments, the weights may be linearly associated with the impedance, temperature, force and/or proximity. For example, if the first electrode has an impedance 30% greater than the second electrode, the first electrode may be have a 30% higher weight assigned to the unipolar signal sensed by the first electrode than the unipolar signal sensed by the second electrode. Alternatively, the weights may be nonlinearly associated with the impedance, temperature, force and/or proximity.

Once the far-field component is determined by the signal processing component 420, the signal processing component 420 may remove the far-field signal from any contacting electrodes to determine a near-field component of the sensed unipolar signal. For example, the signal processing component 420 may subtract the determined far-field signal from the unipolar signal sensed by a contacting electrode to yield the near-field component of a unipolar signal sensed by a contacting electrode.

Additionally or alternatively, sensed signals may be rejected based on a level of tissue contact. For example, when a threshold level of tissue contact for an electrode is exceeded, as determined by the tissue contact component 418, the signal processing component 420 may accept signals received from the electrode. Alternatively, in embodiments, when a threshold level of tissue contact for an electrode does not meet or exceed a threshold, the signal processing component 420 may reject signals received from the electrode.

Once a near-field component of a sensed unipolar signal is determined, the mapping component 422 may perform one or more updates to any unipolar signals. For example, the mapping component 422 may update any electro-anatomical maps based on the calculated near-field signals. Additionally or alternatively, the mapping component 422 may assign an activation time to the near-field component that may be determined based on a peak, max derivative of negative component and/or the like. Additionally or alternatively, the mapping component 422 may determine a voltage amplitude and/or mapping window of the near-field component of the unipolar signal. Additionally or alternatively, the mapping component may determine any fractionated potentials, double potentials and/or late potentials. Additionally or alternatively, lesion maturation may be determined by the mapping component 422 using the near-field signal component of the unipolar signal. In embodiments, only signals that are accepted by the signal processing component 420 may be used by the mapping component 420. In embodiments where the signal processing unit 420 does not accept or reject signals based on a level of contact of the electrode, all sensed signals may be used by the mapping component 420 and/or another method (e.g., filtering signals based on a frequency, etc.) may be used to determine whether a signal is used by the mapping component 422.

In embodiments, any calculations and/or maps determined by the mapping component 422 may be provided to the display device 404 for use by a clinician. Additionally or alternatively, an indication to the clinician about a characteristic of the tip assembly (e.g., tissue contact) and/or the tissue being mapped may be provided to the display device 404. In instances where an output is generated to a display device 404, the mapping component 422 may be operatively coupled to or otherwise in communication with the display device 404. In embodiments, the display device 404 may present various static and/or dynamic representations of information related to the use of the mapping system 402. For example, the display device 404 may present an image representing the target area, an image representing the catheter, an image representing tissue contact of the catheter, notifications relating to tissue contact, and/or information related to EGMs, which may be analyzed by the user and/or by the processor 412 to determine the existence and/or location of arrhythmia substrates within the heart, to determine the location of the catheter within the heart, vasculature and/or other organ, and/or to make other determinations relating to use of the catheter and/or other catheters. In addition or alternatively, the mapping system 402 may include speakers (not shown) and an audio sound and/or notification may be emitted from the speakers when a condition is present or is not present and/or may be progressive (e.g., tissue contact of at least one mapping electrode).

The illustrative operating environment 400 of FIG. 4 is not intended to suggest any limitation as to the scope of use or functionality of embodiments of the present disclosure. The illustrative operating environment 400 also should not be interpreted as having any dependency or requirement related to any single component or combination of components illustrated therein. Additionally, various components depicted in FIG. 4 may be, in embodiments, integrated with various ones of the other components depicted therein (and/or components not illustrated), all of which are considered to be within the ambit of the present disclosure.

Figure 5:
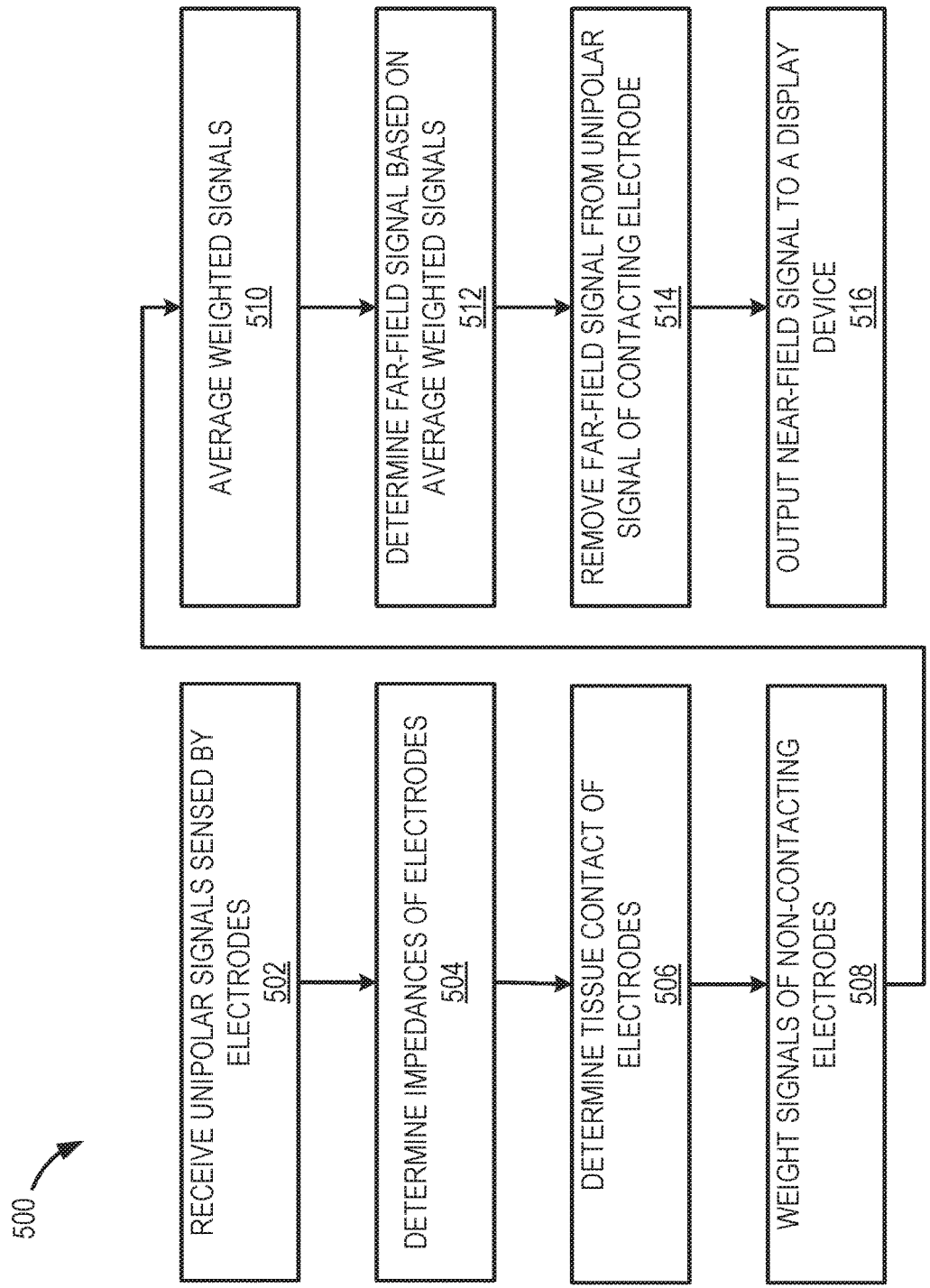
FIG. 5 is a flow diagram depicting an illustrative method for removing far-field signals present in unipolar signals, in accordance with embodiments disclosed herein.

FIG. 5 is a flow diagram depicting an illustrative method 500 for removing far-field signals present in unipolar signals, in accordance with embodiments of the subject matter disclosed herein. According to embodiments, the method 500 may be performed by any number of different aspects of components of the medical system 100 depicted in FIG. 1, the computing device 200 depicted in FIG. 2, the tip assembly 302 depicted in FIG. 3, and/or the operating environment 400 depicted in FIG. 4. For example, in embodiments, the illustrative method 500 may be performed by a processor and/or memory, as described herein.

Embodiments of the method 500 include receiving unipolar signals sensed by electrodes (block 502). In embodiments, the method 500 may include determining whether the received signals represent stable signals. For example, the method 500 may include determining whether it is likely the subject was moving during acquisition of the signals and/or the morphology of the signals are stable, i.e., the rhythm of the signal is stable. If the method 500 determines either there is subject movement and/or the rhythm is not stable, the received unipolar signals may be disregarded and the method 500 may receive new unipolar signals.

The method 500 further includes determining impedances of the electrodes used to sense the unipolar signals (block 504). According to embodiments, determining impedances of electrodes may be performed according to the embodiments discussed above in relation to FIGS. 3 and 4.

As is further shown in FIG. 5, embodiments of the method 500 include determining tissue contact of electrodes (block 506). According to embodiments, determining impedances of electrodes may be performed according to the embodiments discussed above in relation to FIGS. 3 and 4. For example, determining tissue contact of electrodes may be based on the determine impedances. Additionally or alternatively, the determining tissue contact may be based on one or more of the following: amplitude of the sensed unipolar electrical signal, sensed temperature, determined mechanical force, and/or proximity to a proximity sensor of the catheter in embodiments where the catheter is a basket catheter. In embodiments, the method 500 may include weighting signals of the non-contacting electrodes (block 508). In embodiments, weighting signals of the non-contacting electrodes may be based on the determined impedances of the electrodes. In embodiments, the weights assigned to the signals of the non-contacting electrodes may be linearly related to the respective determined impedances of the electrodes.

As shown in FIG. 5, the method 500 may include averaging the weighted signals of the non-contacting electrodes (block 510) and determining a far-field signal component of a unipolar signal sensed by a contacting electrode (block 512). In embodiments, the average weighted signal may be the far-field signal component of the unipolar signal sensed by the contacting electrode. The method 500 may further include removing the far-field signal from the unipolar signal of the contacting electrode (block 514). In embodiments, the far-field signal component may be subtracted from the unipolar signal to yield the near-field signal component of the unipolar signal of the contacting electrode. In embodiments, the method 500 may further include outputting the near-field signal to a display device for use by a physician (block 516).

The illustrative method 500 of FIG. 5 is not intended to suggest any limitation as to the scope of use or functionality of embodiments of the present disclosure. The illustrative method 500 also should not be interpreted as having any dependency or requirement related to any single block or combination of blocks illustrated therein. Additionally, various blocks depicted in FIG. 5 may be, in embodiments, integrated with various ones of the other blocks depicted therein (and/or blocks not illustrated), all of which are considered to be within the ambit of the present disclosure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical system for removing far-field signals from a unipolar electrical signal, the medical system comprising:
   a catheter comprising a plurality of electrodes, each electrode being configured to sense unipolar electrical signals transmitted through tissue; and
   a processing device communicatively coupled to the catheter, the processing device configured to:
      receive the sensed unipolar electrical signals;
      determine an electrode of the plurality of electrodes having a high level of contact with the tissue;
      determine an electrode of the plurality of electrodes having a lower level of contact with the tissue than the electrode having the high level of contact with the tissue;
      determine a sensed near-field electrical signal based on the unipolar electrical signal received from the electrode having the high level of contact and the unipolar electrical signal received from the electrode having the lower level of contact; and
      output the determined near-field electrical signal to a display device.

2. The medical system of claim 1, wherein the electrode of the plurality of electrodes having a lower level of contact comprises more than one electrode of the plurality of electrodes and wherein the processing device is further configured to average the unipolar electrical signals received from the more than one electrode having the lower level of contact.

3. The medical system of claim 2, wherein to average the unipolar electrical signals received from the more than one electrode having the lower level of contact, the processing device is configured to assign weights to each of the unipolar electrical signals received from the more than one electrode having the lower level of contact and average the weighted unipolar electrical signals.

4. The medical system of claim 3, the processing device further configured to determine impedances associated with each electrode of the plurality of electrodes and wherein the weights assigned to the unipolar electrical signals are based on the respective determined impedances associated with each electrode.

5. The medical system of claim 4, wherein the weights have a linear relationship with the respective determined impedances.

6. The medical system of claim 2, wherein to determine the sensed near-field electrical signal, the processing device is configured to subtract the averaged unipolar electrical signal from the unipolar electrical signal received from the electrode having the high level of contact.

7. The medical system of claim 1, wherein the processing device is configured to: determine an electrode's level of contact with the tissue based on at least one of: amplitude of the sensed unipolar electrical signal, measured impedance, sensed temperature, determined mechanical force, and proximity to a proximity sensor of the catheter.

8. The medical system of claim 7, wherein the processing device is configured to: accept or reject a sensed signal based on the determined electrode's level of contact; and include only the accepted signals in an electro-anatomical map.

9. A method removing far-field signals from a unipolar electrical signal, the method comprising:
   receiving sensed unipolar electrical signals from a plurality of electrodes disposed on a distal end of a catheter, wherein the unipolar electrical signals are transmitted through tissue;
   determining an electrode of the plurality of electrodes having a high level of contact with the tissue;
   determine an electrode of the plurality of electrodes having a lower level of contact with the tissue than the electrode having the high level of contact with the tissue;
   determine a sensed near-field electrical signal based on the unipolar electrical signal received from the electrode having the high level of contact and the unipolar electrical signal received from the electrode having the lower level of contact; and
   output the determined near-field electrical signal to a display device.

10. The method of claim 9, wherein the electrode of the plurality of electrodes having a lower level of contact comprises more than one electrode of the plurality of electrodes and the method further comprising averaging the unipolar electrical signals received from the more than one electrode having the lower level of contact.

11. The method of claim 10, wherein averaging the unipolar electrical signals received from the more than one electrode having the lower level of contact comprises assigning weights to each of the unipolar electrical signals received from the more than one electrode having the lower level of contact and average the weighted unipolar electrical signals.

12. The method of claim 11, further comprising determining impedances associated with each electrode of the plurality of electrodes and wherein the weights assigned to the unipolar electrical signals are based on the respective determined impedances associated with each electrode.

13. The method of claim 12, wherein the weights have a linear relationship with the respective determined impedances.

14. The method of claim 10, wherein determining the sensed near-field electrical signal comprises subtracting the averaged unipolar electrical signal from the unipolar electrical signal received from the electrode having the high level of contact.

15. The method of claim 9 further comprising: determining an electrode's level of contact with the tissue based on at least one of: amplitude of the sensed unipolar electrical signal, measured impedance, sensed temperature, determined mechanical force, and proximity to a proximity sensor of the catheter.

16. The method of claim 15, wherein the electrode having the high level of contact is the electrode having a higher impedance than other electrodes of the plurality of electrodes.

17. A non-transitory computer-readable medium comprising executable instructions that when executed by one or more processors of a medical system cause the one or more processors to:
receive sensed unipolar electrical signals from a plurality of electrodes disposed on a distal end of a catheter, wherein the unipolar electrical signals are transmitted through tissue;
determine an impedance associated with each electrode of the plurality of electrodes;
determine, using the determined impedances, an electrode of the plurality of electrodes having a high level of contact with the tissue;
determine, using the determined impedances, an electrode of the plurality of electrodes having a lower level of contact with the tissue than the electrode having the high level of contact with the tissue;
determine, using the unipolar electrical signal sensed by the electrode having the lower level of contact, a far-field component of the unipolar electrical signal sensed by the electrode having a high level of contact;
remove the far-field component of the unipolar electrical signal sensed by the electrode having the high level of contact to determine the near-field component of the unipolar electrical signal sensed by the electrode having the high level of contact; and
output the determined near-field electrical signal to a display device.

18. The non-transitory computer-readable medium of claim 17, wherein the electrode of the plurality of electrodes having a lower level of contact comprises more than one electrode of the plurality of electrodes and wherein the executable instructions comprise instructions that cause the one or more processors to: average the unipolar electrical signals received from the more than one electrode having the lower level of contact.

19. The non-transitory computer-readable medium of claim 18, wherein to average the unipolar electrical signals received from the more than one electrode having the lower level of contact, the executable instructions comprise instructions that cause the one or more processors to: assign weights to each of the unipolar electrical signals received from the more than one electrode having the lower level of contact and average the weighted unipolar electrical signals.

20. The non-transitory computer-readable medium of claim 19, wherein the weights have a linear relationship with the respective determined impedances.

* * * * *